US012693292B2

(12) United States Patent
Hariyama et al.

(10) Patent No.: US 12,693,292 B2
(45) Date of Patent: Jul. 28, 2026

(54) IMMUNOCHROMATOGRAPHY ASSAY KIT

(71) Applicants: NATIONAL UNIVERSITY CORPORATION HAMAMATSU UNIVERSITY SCHOOL OF MEDICINE, Shizuoka (JP); NTN Corporation, Osaka (JP)

(72) Inventors: Takahiko Hariyama, Hamamatsu (JP); Hideya Kawasaki, Hamamatsu (JP); Hiroaki Ohba, Iwata (JP)

(73) Assignees: NATIONAL UNIVERSITY CORPORATION HAMAMATSU UNIVERSITY SCHOOL OF MEDICINE, Shizuoka (JP); NTN Corporation, Osaka (JP)

( * ) Notice: Subject to any disclaimer, the term of this patent is extended or adjusted under 35 U.S.C. 154(b) by 730 days.

(21) Appl. No.: 18/034,342

(22) PCT Filed: Nov. 2, 2021

(86) PCT No.: PCT/JP2021/040352
§ 371 (c)(1),
(2) Date: Apr. 27, 2023

(87) PCT Pub. No.: WO2022/097628
PCT Pub. Date: May 12, 2022

(65) Prior Publication Data
US 2023/0408511 A1 Dec. 21, 2023

(30) Foreign Application Priority Data

Nov. 5, 2020 (JP) ................................. 2020-185343
Nov. 5, 2020 (JP) ................................. 2020-185344

(51) Int. Cl.
*G01N 33/543* (2006.01)

(52) U.S. Cl.
CPC .............................. *G01N 33/54388* (2021.08)

(58) Field of Classification Search
CPC ................................................ G01N 33/54388
See application file for complete search history.

(56) References Cited

U.S. PATENT DOCUMENTS

| | | | |
|---|---|---|---|
| 2011/0132109 A1 | 6/2011 | Delaage | |
| 2011/0244597 A1 | 10/2011 | Tsukada et al. | |
| 2012/0184462 A1* | 7/2012 | O'Farrell | G01N 33/54388 |
| | | | 506/15 |

FOREIGN PATENT DOCUMENTS

| | | |
|---|---|---|
| CN | 104749359 A | 7/2015 |
| CN | 108535472 A | 9/2018 |

(Continued)

OTHER PUBLICATIONS

Rivas, Lourdes, et al. "Improving sensitivity of gold nanoparticle-based lateral flow assays by using wax-printed pillars as delay barriers of microfluidics." Lab on a Chip 14.22 (2014): 4406-4414. (Year: 2014).*

(Continued)

*Primary Examiner* — Bao-Thuy L Nguyen
*Assistant Examiner* — Christopher Evans
(74) *Attorney, Agent, or Firm* — Rimon P.C.

(57) ABSTRACT

An immunochromatography assay kit includes a specimen dropping portion to which a specimen is dropped, a conjugate portion to which a labeled antibody having a property of binding to a detection target in the specimen is immobilized, and a plurality of detection portions to which a capture antibody having a property of binding to the detection target is immobilized. The specimen dropping portion, the conjugate portion, and the plurality of detection portions are formed on a porous member. An outer shape of each detection portion is a dot shape.

16 Claims, 14 Drawing Sheets

(56)            References Cited

FOREIGN PATENT DOCUMENTS

| EP | 1365248 A2 | 11/2003 |
| EP | 2352028 A1 | 8/2011 |
| EP | 2554992 A1 | 2/2013 |
| JP | 2011-516875 A | 5/2011 |
| JP | 2013-113633 A | 6/2013 |
| JP | 2016-166878 A | 9/2016 |
| JP | 2019-118884 A | 7/2019 |
| WO | 2008/105814 A2 | 9/2008 |
| WO | 2010/061772 A1 | 6/2010 |
| WO | 2010/120951 A1 | 10/2010 |

OTHER PUBLICATIONS

Irina V. Safenkova et al., "Multiarray on a test strip (MATS): rapid multiplex immunodetection of priority potato pathogens", Analytical and Bioanalytical Chemistry, vol. 408, No. 22, Mar. 23, 2016, pp. 6009-6017.

Park, J. et al., "Multiplex detection of pathogens using an immunochromatographic assay strip", Biochip Journal, vol. 4, No. 4, Nov. 20, 2010, pp. 305 312.

Taranova, N.A. et al., "Integration of lateral flow and microarray technologies for multiplex immunoassay: application to the determination of drugs of abuse", Mikrochimica Acta, vol. 180, No. 11 12, Jul. 13, 2013, pp. 1165 1172.

Thibault, C. et al., "Direct microcontact printing of oligonucleotides for biochip applications", Journal of Nanobiotechnology, vol. 3, No. 1, Jul. 1, 2005.

International Search Report issued in International Application No. PCT/JP2021/040352 dated Jan. 18, 2022, with English translation.

* cited by examiner

IMMUNOCHROMATOGRAPHY ASSAY KIT

CROSS-REFERENCE OF RELATED APPLICATIONS

This application is the U.S. National Phase under 35 U.S.C. § 371 of International Patent Application No. PCT/JP2021/040352, filed on Nov. 2, 2021, which in turn claims the benefit of Japanese Patent Application No. 2020-185343, filed on Nov. 5, 2020, and Japanese Patent Application No. 2020-185344, filed Nov. 5, 2020, the entire disclosures of which Applications are incorporated by reference herein.

TECHNICAL FIELD

The present invention relates to an immunochromatography assay kit.

BACKGROUND ART

Immunochromatography is currently implemented in society as a diagnostic aid for various diseases with influenza viruses as a center. A principle of the immunochromatography uses an antigen-antibody reaction, and is widely used in medical practice due to simplicity and effectiveness.

In the conventional immunochromatography, presence or absence of color development in a detection portion of an immunochromatography assay kit (also referred to as development support or chromatographic medium) is visually observed. Specifically, when a detection target bound to a labeled antibody is captured by a capture antibody immobilized on the detection portion and sufficiently accumulated on the detection portion, the color development derived from the labeled antibody is visually checked.

WO 2010/061772 (PTL 1) discloses an immunochromatography assay kit in which the detection portion is formed in a size greater than or equal to several mm that can be visually determined.

CITATION LIST

Patent Literature

PTL 1: WO 2010/061772

SUMMARY OF INVENTION

Technical Problem

In the conventional immunochromatography assay kit as described above, because the color development derived from the labeled antibody is visually checked, a sufficient area is required to be provided in order to prevent erroneous determination, and as a result, the area of the detection portion is greater than or equal to several mm². For this reason, a large number of capture antibodies greater than or equal to some extent is required to be immobilized on the detection portion to capture the antigen, and it is difficult to reduce the amount of expensive capture antibodies used, and it is difficult to reduce the cost.

A main object of the present invention is to provide a low-cost immunochromatography assay kit capable of suppressing the use amount of the capture antibody as compared with the conventional immunochromatography assay kit.

Solution to Problem

An immunochromatography assay kit according to an embodiment of the present invention includes a specimen dropping portion to which a specimen is dropped, a conjugate portion on which a labeled antibody having a property of binding to a detection target in the specimen is immobilized, and at least one detection portion to which a capture antibody having a property of binding to a detection target is attached. The specimen dropping portion, the conjugate portion, and the at least one detection portion are formed on a porous member. The capture antibody having the property of binding to the detection target is immobilized to the at least one detection portion. The outer shape of at least one detection portion is a dot shape.

In the immunochromatography assay kit according to the embodiment, at least one recess may be formed in the porous member. The at least one detection portion includes a bottom surface of the at least one recess.

An immunochromatography assay kit according to another embodiment of the present invention includes a specimen dropping portion to which a specimen is dropped, a conjugate portion to which a labeled antibody having a property of binding to a detection target in the specimen is attached, and at least one detection portion to which a capture antibody having a property of binding to a detection target is attached. The specimen dropping portion, the conjugate portion, and the at least one detection portion are formed on a porous member. At least one recess is formed in the porous member. The at least one detection portion includes a bottom surface of the at least one recess.

In the immunochromatography assay kit according to the one embodiment and the other embodiment, preferably a width of at least one detection portion is less than 1 mm.

In the immunochromatography assay kit according to the one embodiment and the other embodiment, an outer diameter of the at least one detection portion may be less than or equal to 100 μm.

In the immunochromatography assay kit according to the embodiment, the at least one detection portion may be a plurality of detection portions.

In the immunochromatography assay kit according to another embodiment, the at least one detection portion may be a plurality of detection portions, and the at least one recess may be a plurality of recesses. Each of the plurality of detection portions includes a bottom surface of one of the plurality of recesses.

In the immunochromatography assay kit according to the one embodiment and the other embodiment, the plurality of detection portions may be arranged one-dimensionally or two-dimensionally.

In the immunochromatography assay kit according to the one embodiment and the other embodiment, a shortest distance between two adjacent detection portions among the plurality of detection portions may be less than 1 mm.

In the immunochromatography assay kit according to the one embodiment and another embodiment, the plurality of detection portions may include a first detection portion to which a first capture antibody having a property of binding to a first type of detection target is immobilized and a second detection portion to which a second capture antibody having a property of binding to a second type of detection target is immobilized.

In the immunochromatography assay kit according to the one embodiment and the other embodiment, the specimen dropping portion, the conjugate portion, and the at least one detection portion may be formed on a single porous member.

In the immunochromatography assay kit according to the one embodiment and the other embodiment, the specimen dropping portion, the conjugate portion, and the at least one detection portion may be formed on a plurality of porous members.

Advantageous Effects of Invention

According to the present invention, the low-cost immunochromatography assay kit capable of preventing the use amount of the capture antibody as compared with the conventional immunochromatography assay kit can be provided.

BRIEF DESCRIPTION OF DRAWINGS

FIG. 8 is a side view illustrating the application unit of the application device in FIG. 6.

FIG. 11 is a partially enlarged plan view illustrating a modification of the detection portion in FIG. 2.

DESCRIPTION OF EMBODIMENTS

Figure 1:
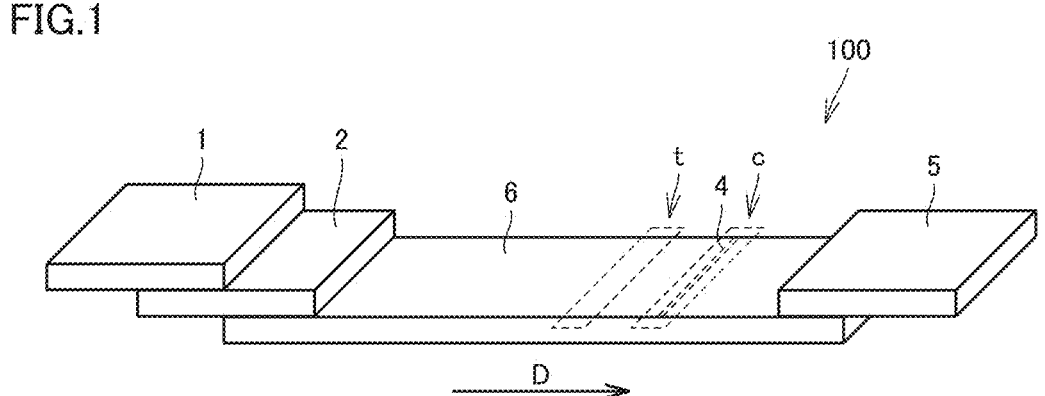
FIG. 1 is a perspective view illustrating an immunochromatography assay kit according to a first embodiment.

With reference to the drawings, an embodiment as an example of the present invention will be described below. In the following drawings, the same or corresponding component is designated by the same reference numeral, and overlapping description will be omitted.

First Embodiment

<Immunochromatography Assay Kit>

Figure 2:
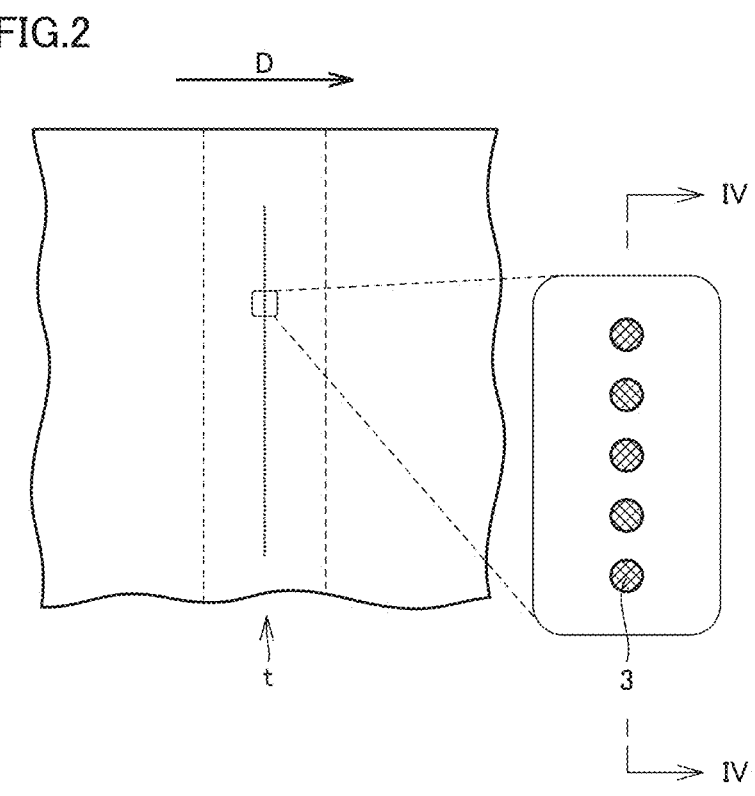
FIG. 2 is a partially enlarged plan view illustrating a detection portion of the immunochromatography assay kit in FIG. 1.

As illustrated in FIGS. 1 and 2, an immunochromatography assay kit 100 according to a first embodiment mainly includes a specimen dropping portion 1, a conjugate portion 2, a detection region t including a plurality of detection portions 3, a control region c including a control portion 4, and an absorption portion 5. As illustrated in FIGS. 1 and 2, specimen dropping portion 1, conjugate portion 2, detection region t, control region c, and absorption portion 5 are arranged in the above-described order along a developing direction D.

Specimen dropping portion 1 is a section to which a specimen is dropped. Specimen dropping portion 1 is formed of a porous member such as a glass fiber pad, a cellulose fiber pad, and a polyester pad.

Conjugate portion 2 is a section on which a labeled antibody having a property of binding to a detection target in a specimen is immobilized. The labeled antibody is a conjugate of an antibody that specifically recognizes and binds to a first section (first epitope) of the detection target and a labeling substance. The antibody can be arbitrarily selected according to the detection target. The labeling substance can be arbitrarily selected from labeling substances used in conventional immunochromatography. For example, the labeling substance includes at least one selected from a group consisting of metal nanoparticles (metal fine particles), latex fine particles, organic polymer fine particles, inorganic fine particles, and coloring fine particles such as liposomes containing a coloring agent. For example, the labeling substance includes at least one selected from a group consisting of noble metal nanoparticles such as gold nanoparticles, platinum nanoparticles, platinum-gold nanoparticles, and silver nanoparticles, titanium nanoparticles, iron nanoparticles, nickel nanoparticles, and cadmium nanoparticles as metal nanoparticles. The metal nanoparticles may be colloidal metal nanoparticles having a particle size greater than or equal to 1 nm and less than or equal to 100 nm. For example, conjugate portion 2 is adjusted by applying a suspension containing the labeled antibody to the porous member such as the glass fiber pad, the cellulose fiber pad, or the polyester pad, and drying the porous member.

A detection region t is disposed on an opposite side of specimen dropping portion 1 with respect to conjugate portion 2 in developing direction D. Detection region t is formed on a carrier 6 including the porous member. The detection region t includes a plurality of detection portions 3. Each detection portion 3 is connected to specimen dropping portion 1 through conjugate portion 2. Each detection portion 3 is disposed on the opposite side of specimen dropping portion 1 with respect to conjugate portion 2 in developing direction D. Each detection portion 3 is a section on which a capture antibody having a property of binding to the detection target is immobilized. The capture antibody is an antibody that specifically recognizes and binds to a second section (second epitope) different from the first section of the detection target. From a different point of view, the capture antibody has a property of binding to an assay target bound to the labeling substance. The capture antibody can be arbitrarily selected according to the detection target.

As illustrated in FIG. 2, a planar outer shape of each detection portion 3 is a dot shape. A dot width of each detection portion 3 is a minimum size that can be visually observed or a size that cannot be visually observed but can be observed with a microscope. For example, the dot width of each detection portion 3 is less than 1 mm. Preferably, the dot width of each detection portion 3 is equivalent to a view field such as an electron microscope in which a labeling substance having the size less than or equal to 1 μm binding to the labeled antibody can be directly observed. For example, the dot width of each detection portion 3 is less than or equal to 100 μm.

The width of the detection portion 3 is measured as follows. First, a specimen containing the sufficient detection target is dropped onto specimen dropping portion 1, and an antigen-antibody reaction is developed on immunochromatography assay kit 100. Subsequently, an electron microscope image of detection portion 3 is acquired according to an assay method described later. When detection portion 3 includes a bottom surface 7A of a recess 7 like immunochromatography assay kit 100 of the first embodiment, the electron microscope image acquired by focusing on bottom surface 7A is used. Subsequently, the outer shape of the region where the labeled antibody is observed in the image is specified as the outer shape of detection portion 3.

Figure 3:
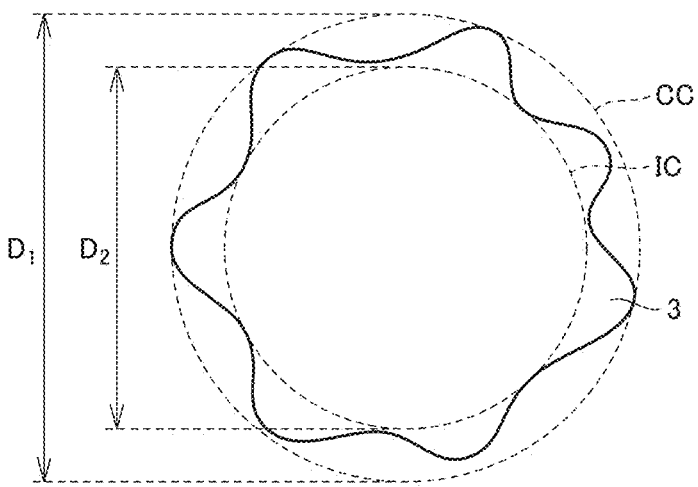
FIG. 3 is a partially enlarged view illustrating a width of the detection portion.

Subsequently, the width of the outer shape of detection portion 3 is measured. As illustrated in FIG. 3, when an outline of the region where the labeled antibody is observed is wavy inside and outside, a diameter D1 of a circumscribed circle CC of the outline and a diameter D2 of an inscribed circle IC of the outline are calculated by image processing, and an intermediate value between diameter D1 and diameter D2 is defined as the width of the outline of detection portion 3.

Detection portions 3 in FIG. 2 are arranged at intervals in a direction intersecting (for example, orthogonal to) developing direction D. Each detection portion 3 is one-dimensionally arranged in the direction intersecting (for example, orthogonal to) developing direction D. For example, the distance between two adjacent detection portions 3 is less than 1 mm.

The planar outer shape of each detection portion 3 is not particularly limited as long as detection portion 3 has a dot shape, and for example, has a circular shape. The planar outer shape of each detection portion 3 may be an elliptical shape, a square shape, a rectangular shape, or the like.

Figure 4:
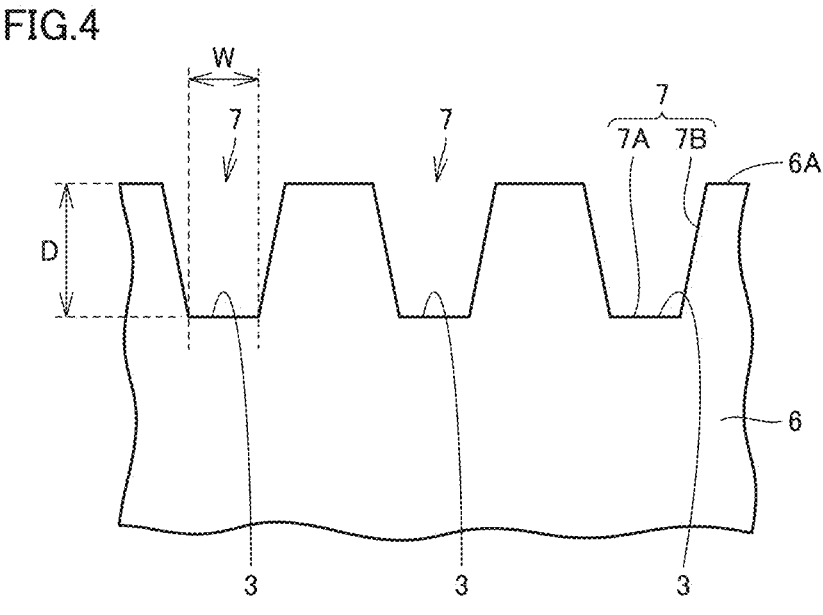
FIG. 4 is a partially enlarged sectional view as viewed from an arrow IV-IV in FIG. 2.

As illustrated in FIG. 4, a plurality of recesses 7 are formed in detection region t of carrier 6. Each recess 7 is recessed with respect to an upper surface of carrier 6. Each recess 7 has bottom surface 7A and a wall surface 7B connecting bottom surface 7A and the upper surface of carrier 6, and an opening of an upper surface 6A and bottom surface 7A have a dot shape. In the section in FIG. 4, bottom surface 7A and wall surface 7B form an obtuse angle. In other words, the sectional shape of each recess 7 in FIG. 4 has a tapered shape in which the interval between opposing wall surfaces 7B becomes narrower as approaching bottom surface 7A, but an opening diameter of upper surface 6A and the diameter of bottom surface 7A may be equal to each other. The width of bottom surface 7A of each recess 7 is a minimum size that can be checked by the visual observation, for example, less than 1 mm. Preferably, the width of bottom surface 7A of each recess 7 is desirably equal to the view field such as the electron microscope in which the labeling substance having the size of less than or equal to 1 μm bound to the labeled antibody is directly observed. For example, the dot width of each bottom surface 7A is less than or equal to 100 μm. The depth of each bottom surface 7A is deeper than a focal depth of the electron microscope. For example, the depth of each bottom surface 7A is greater than or equal to 10 μm.

For example, the planar outer shape of each bottom surface 7A is a circular shape. The planar outer shape of each bottom surface 7A may be an elliptical shape, a square shape, a rectangular shape, or the like.

Each detection portion 3 includes bottom surface 7A of each recess 7. Each detection portion 3 is formed in each recess 7 of carrier 6. For example, detection portions 3 and recesses 7 are simultaneously formed on carrier 6. A method for simultaneously forming detection portion 3 and recess 7 on carrier 6 will be described in detail described later in a method for manufacturing the immunochromatography assay kit.

Control region c is disposed on the opposite side of conjugate portion 2 with respect to detection region t in developing direction D. Control region C includes control portion 4. Control portion 4 is a section on which a control antibody that binds to the labeled antibody is immobilized. The planar outer shape of control portion 4 may be any shape, and for example, is a linear shape.

Control portion 4 is formed on carrier 6. Control portion 4 is disposed on the opposite side of conjugate portion 2 with respect to detection portion 3 in developing direction D.

In FIGS. 1 and 2, for convenience of description, ranges of detection area t and control area c are indicated by a broken line. In the actual immunochromatography assay kit, for example, the broken line is not illustrated.

Absorption portion 5 is a section that absorbs a surplus specimen or the like after the development. Absorption portion 5 is formed of the porous member such as the glass fiber pad, the cellulose fiber pad, or the polyester pad. Absorption portion 5 is disposed on the side opposite to detection region t with respect to control region c in developing direction D.

The planar outer shape of carrier 6 is a rectangular shape. Carrier 6 has a longitudinal direction along developing direction D and a lateral direction orthogonal to developing direction D. The material constituting carrier 6 may be any porous material, and for example, includes at least one of nitrocellulose and polyvinylidene fluoride (PVDF). That is, in immunochromatography assay kit 100 of the first embodiment, the plurality of detection portions 3 and the plurality of control portions 4 are formed on a porous member separate from the porous member constituting specimen dropping portion 1, conjugate portion 2, and absorption portion 5. For example, the porous member constituting specimen dropping portion 1 is bonded to the porous member constituting conjugate portion 2. For example, each of the porous members constituting conjugate portion 2 and absorption portion 5 is bonded to each of the porous members constituting carrier 6.

Specimen dropping portion 1, conjugate portion 2, detection portion 3, control portion 4, absorption portion 5, and carrier 6 may be fixed on a base material (also referred to as a backing sheet) (not illustrated) using an adhesive or an adhesive sheet. Carrier 6 may be a thin film formed on the base material.

<Assay Method Using Immunochromatography Assay Kit>

In an assay method using the immunochromatography assay kit, detection portion 3 after the antigen-antibody reaction on the immunochromatography assay kit is observed using the electron microscope. Hereinafter, the antigen-antibody reaction on the immunochromatography assay kit will be described.

First, the specimen is dropped into specimen dropping portion 1. The dropped specimen flows along developing direction D due to a capillary phenomenon. The detection target in the specimen binds to the labeled antibody in conjugate portion 2. The conjugate of the detection target and the labeled antibody moves along developing direction D together with the labeled antibody not bound to the detection target due to the capillary phenomenon. The detection target bound to the labeled antibody is bound to the capture antibody in detection portion 3. Thus, the labeled antibody bound to the detection target is accumulated in detection portion 3. The labeling substance bound to the labeled antibody in detection portion 3 is directly observed using the electron microscope. Furthermore, the labeled antibody not bound to the detection target binds to the control antibody in control portion 4. Thus, the labeled antibody not bound to the detection target is captured by control portion 4. The labeling substance bound to the labeled antibody in control portion 4 is directly observed using the electron microscope. The excessive specimen flowing downstream of control portion 4 in developing direction D is absorbed by absorption portion 5.

For example, the assay method using the immunochromatography assay kit is performed by the following procedure.

First, after dropping the specimen into specimen dropping portion 1, the auxiliary liquid is dropped after a designated time elapses.

The auxiliary liquid has conductivity preventing electrification and generation of heat contributing to sharpness of the image and/or a property of forming a film by polymerization under measurement conditions of the electron microscope. The auxiliary liquid contains glycerin and a substitute for glycerin, at least one compound selected from polysorbates such as polysorbate 20, polysorbate 40, polysorbate 60, polysorbate 65, polysorbate 80, and polysorbate 85 and polysorbate substitutes as essential components, and at least one compound selected from monosaccharides, disaccharides, salts, and buffers as an optional component.

Subsequently, detection portion 3 is observed using the electron microscope. Specifically, first, carrier 6 is set in a chamber of the electron microscope. Subsequently, detection portion 3 is searched while the upper surface of carrier 6 is observed. In immunochromatography assay kit 100, defocus due to the distance between the upper surface of carrier 6 and bottom surface 7A is observed in the microscopic image (bright-field image) of the electron microscope. Accordingly, recess 7 can be searched in the microscopic image by checking the presence or absence of the defocus, so that detection portion 3 can be easily searched in the image. Thereafter, by focusing the image on bottom surface 7A, the image can be focused on detection portion 3. Subsequently, the electron microscope image is captured, and the number of labeling substances in the image is measured. The outline of the labeling substance can be clearly identified in the electron microscope image, so that the number of labeling substances in the image can be measured. When the number of measured labeling substances exceeds a predetermined criterion, it is determined that the detection target exists in the specimen (that is, "positive").

For example, the observation and the measurement are similarly performed on the plurality of detection portions 3. In this case, for example, an average value, a maximum value, a minimum value, and the like of the number of labeling substances in the same visual field of each detection portion 3 are calculated, any one of these calculated values is set as an evaluation value, and the number of labeling substances is determined as "positive" when the evaluation value exceeds a predetermined determination criterion.

<Method for Manufacturing Immunochromatography Assay Kit>

Figure 5:
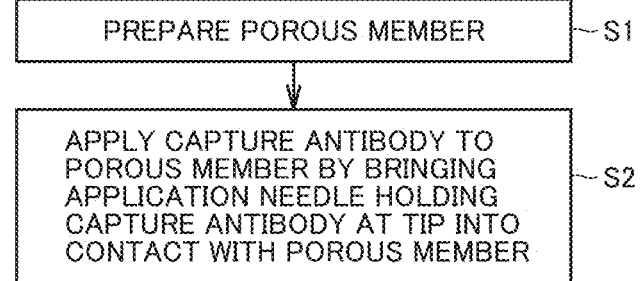
FIG. 5 is a flowchart illustrating a method for manufacturing the immunochromatography assay kit of the first embodiment.

An example of the method for manufacturing immunochromatography assay kit 100 will be described below. As illustrated in FIG. 5, the method for manufacturing immunochromatography assay kit 100 includes a process (S1) of preparing carrier 6 and a process (S2) of forming the plurality of detection portions 3 on prepared carrier 6.

In the process of preparing carrier 6, carrier 6 in which control portion 4 is formed on the upper surface or carrier 6 in which control portion 4 is not formed on the upper surface is prepared.

In the process of forming the plurality of detection portions 3, the capture antibody is applied in the dot shape to the upper surface of carrier 6 using an application needle 21 (see FIG. 10) holding the capture antibody at a tip. The diameter (hereinafter, referred to as a tip diameter) of the tip of application needle 21 is less than 1 mm. In this process, recess 7 is formed on carrier 6 using application needle 21, and at the same time, the capture antibody is applied to bottom surface 7A of recess 7. That is, application needle 21 holding the capture antibody at the tip is further pushed into carrier 6 after coming into contact with the upper surface of carrier 6. In this process, the application device in FIGS. 6 to 10 is used. The configuration of the application device will be described later.

In this manner, carrier 6 including the plurality of detection portions 3 is formed. When control portion 4 is formed on carrier 6, conjugate portion 2 and absorption portion 5 are connected to carrier 6, and specimen dropping portion 1 is connected to conjugate portion 2, whereby immunochromatography assay kit 100 is manufactured. When control portion 4 is not formed on carrier 6, control portion 4 is formed on carrier 6. Thereafter, conjugate portion 2 and absorption portion 5 are connected to carrier, and specimen dropping portion 1 is further connected to conjugate portion 2, whereby immunochromatography assay kit 100 is manufactured. In the method for manufacturing immunochromatography assay kit 100, each of specimen dropping portion 1, conjugate portion 2, control portion 4, and absorption portion 5 can be formed in the same manner as in the conventional immunochromatography assay kit.

<Configuration of Application Device>

An example of the application device used to form the plurality of detection portions 3 in the method for manufacturing immunochromatography assay kit 100 will be described below.

Figure 6:
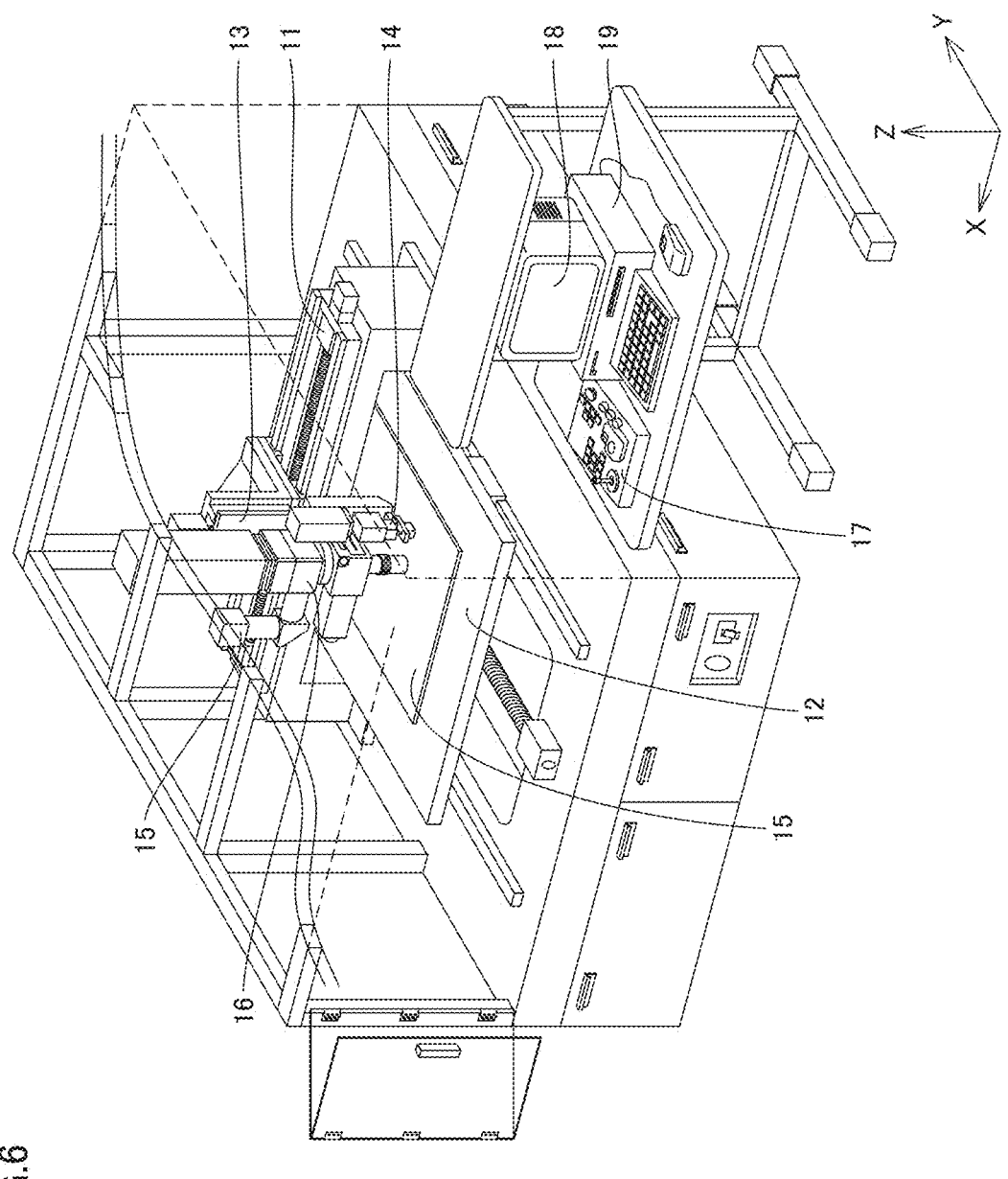
FIG. 6 is a perspective view illustrating an application device used in the method for manufacturing the immunochromatography assay kit of the first embodiment.

As illustrated in FIG. 6, the application device of the first embodiment mainly includes an X-axis table 11, a Y-axis table 12, a Z-axis table 13, an application mechanism 14, an observation optical system 15, a CCD camera 16, and a control portion. For example, X-axis table 11, Y-axis table 12, Z-axis table 13, application mechanism 14, observation optical system 15, and CCD camera 16 are disposed inside a processing chamber. The control portion includes an operation panel 17, a monitor 18, and a control computer 19. For example, operation panel 17, monitor 18, and control computer 19 are disposed outside the processing chamber.

Y-axis table 12 is movable in the Y-axis direction, and carrier 6 can be mounted on Y-axis table 12. For example, a guide rail extending along Y-axis direction is fixed to the bottom of the processing chamber. A guide portion movable along the guide rail is connected to the lower surface of Y-axis table 12. An upper surface of Y-axis table 12 is a mounting surface on which carrier 6 is mounted. A structure straddling Y-axis table 12 in the X-axis direction is fixed to the bottom of the processing chamber.

X-axis table 11 is disposed on the structure installed so as to straddle Y-axis table 12 in the X-axis direction. The moving body to which Z-axis table 13 is connected is installed on X-axis table 11 so as to be movable in the X-axis direction. The moving body is movable in the X-axis direction using, for example, a ball screw. X-axis table 11 is fixed to the bottom surface of the processing chamber through the structure. For this reason, Y-axis table 12 described above is movable in the Y-axis direction with respect to X-axis table 11.

Z-axis table 13 is installed on the moving body connected to X-axis table 11 as described above. Observation optical system 15 and application mechanism 14 are connected to Z-axis table 13. Observation optical system 15 is used to observe the application position on carrier 6. The CCD camera converts the observed image into an electric signal. Z-axis table 13 holds observation optical system 15 and application mechanism 14 so as to be movable in the Z-axis direction.

Operation panel 17, monitor 18, and control computer 19 are used to control Y-axis table 12, X-axis table 11, Z-axis table 13, observation optical system 15, and application mechanism 14. Operation panel 17 is used to input a command to control computer 19. Monitor 18 displays image data converted by CCD camera 16 described above and output data from control computer 19.

<Configuration of Application Mechanism 14>

Figure 7:
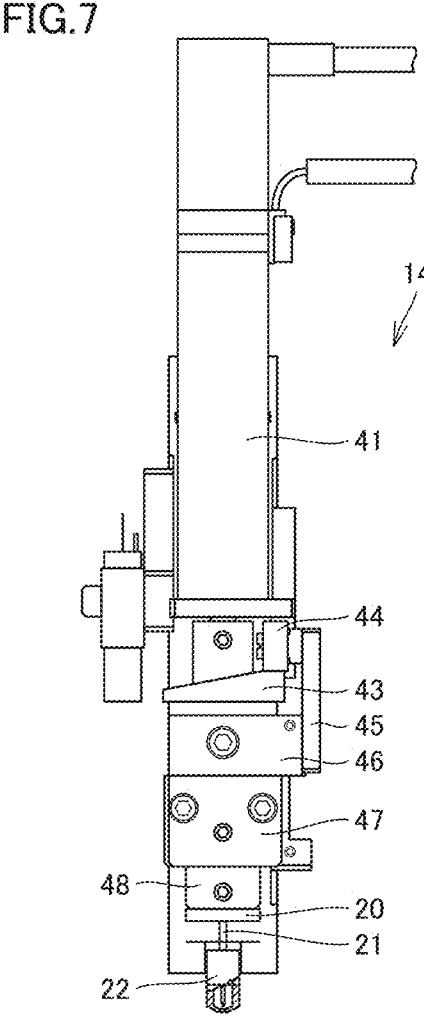
FIG. 7 is a front view illustrating an application unit of the application device in FIG. 6.
Figure 8:
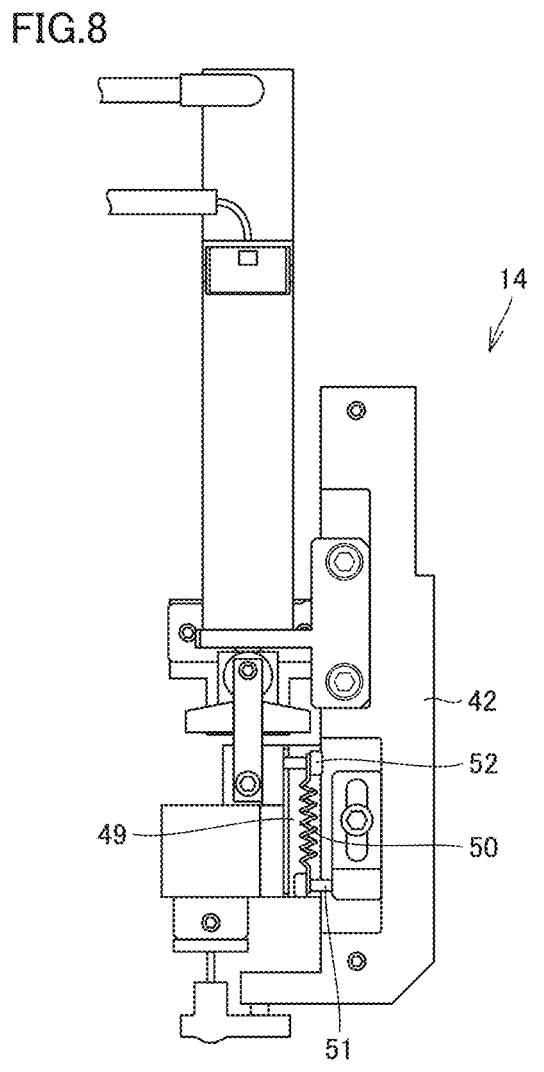

A detailed configuration of application mechanism 14 in FIG. 6 will be described below. As illustrated in FIGS. 7 and 8, application mechanism 14 mainly includes a servomotor 41, a frame 42, a cam 43, a bearing 44, a cam connection plate 45, a movable portion 46, an application needle holder 20, application needle 21 held by application needle holder 20, and an application material container 22. Servomotor 41 is installed such that a rotation shaft extends in a direction along the Z-axis direction in FIG. 6. Servomotor 41 is held on frame 42. Cam 43 is connected to the rotation shaft of servomotor 41. Cam 43 is rotatable about the rotation shaft of servomotor 41.

Cam 43 includes a center portion connected to the rotation shaft of servomotor 41 and a flange portion connected to one end of the center portion. The upper surface of the flange portion (the surface on the side of servomotor 41) is a cam surface. The cam surface is formed in an annular shape along the outer periphery of the center portion, and formed in a slope shape such that the distance from the bottom surface of the flange portion varies. Specifically, the cam surface includes an upper end flat region having the longest distance from the bottom surface of the flange portion, a lower end flat region having the shortest distance from the bottom surface of the flange portion, and a slope region connecting the upper end flat region and the lower end flat region. The upper end flat region is disposed spaced apart from the lower end flat region in the circumferential direction with respect to the rotation shaft.

Bearing 44 includes an outer ring disposed so as to be in contact with the cam surface of cam 43 and an inner ring connected to cam connection plate 45. As illustrated in FIG. 7, bearing 44 is disposed in a specific direction (right side of servomotor 41) as viewed from cam 43. Bearing 44 is biased to the cam surface of cam 43 by a spring 50 described later. Therefore, when cam 43 rotates, bearing 44 is held while the outer peripheral surface of the outer ring is in contact with the cam surface. Cam connection plate 45 has one end connected to the inner ring of bearing 44 and the other end fixed to movable portion 46. An application needle holder fixing portion 47 and an application needle holder accommodation portion 48 are connected to movable portion 46.

A fixing pin 51 is installed on frame 42. A fixing pin 52 is installed in movable portion 46. One end of spring 50 is connected to fixing pin 51, and the other end of spring 50 is connected to fixing pin 52. Movable portion 46 is in the state of being subjected to tensile force toward application material container 22 by spring 50. Tensile force of spring 50 acts on bearing 44 through movable portion 46 and cam connection plate 45. This tensile force of spring 50 keeps bearing 44 pressed against the cam surface of cam 43.

Movable portion 46, application needle holder fixing portion 47, and application needle holder accommodation portion 48 are connected to a linear guide 49 installed on frame 42. Linear guide 49 is disposed so as to extend in the Z-axis direction. Consequently, movable portion 46, application needle holder fixing portion 47, and application needle holder accommodation portion 48 are movable along the Z-axis direction.

Application needle holder 20 is housed in application needle holder accommodation portion 48. Application needle holder 20 includes application needle 21. Application needle 21 is disposed so as to protrude from application needle holder 20 on the lower surface of application needle holder 20. The extending direction of application needle 21 is along a gravity direction (Z-axis direction in FIG. 6). For example, the shape of the tip of application needle 21 is a truncated cone shape. A tip diameter of application needle 21 in the radial direction with respect to the central axis is less than 1 mm. Preferably, the tip diameter of application needle 21 is less than or equal to 100 μm.

Figure 9:
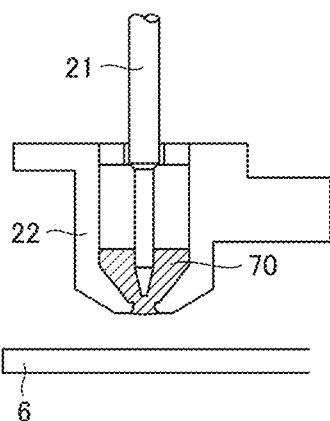
FIG. 9 is a front view illustrating operation of the application unit of the application device in FIG. 6.
Figure 10:
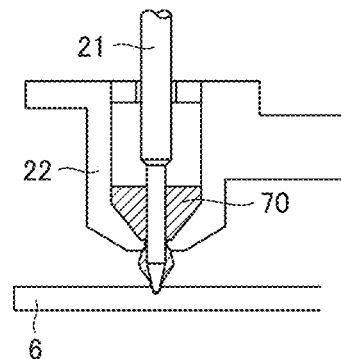
FIG. 10 is a front view illustrating the operation of the application unit of the application device in FIG. 6.

Application material container 22 is disposed below application needle holder 20. A space storing application material 70 is formed inside application material container 22. As illustrated in FIGS. 9 and 10, a first hole and a second hole connecting the space and the outside are made in a bottom and an upper portion of application material container 22. The shape of each of the first hole and the second hole may be any shape, and for example, is a circular shape. The first hole and the second hole are provided so as to overlap each other in the extending direction of application needle 21. Application material 70 contains the capture antibody.

Application needle holder 20 and application needle 21 move up and down with respect to application material container 22 along with the movement of application needle holder accommodation portion 48 in the Z-axis direction. Thus, the first state in which the tip of application needle 21 is immersed in application material 70 stored in application material container 22 and the second state in which the tip passes through a hole made in the bottom of application material container 22 and protrudes downward from the bottom surface of application material container 22 are switched.

<Operation of Application Device>

The operation of the application device in the process of forming the plurality of detection portions 3 of the method for manufacturing the immunochromatography assay kit will be described below. First, carrier 6 is mounted on Y-axis table 12. Subsequently, the first state in which the tip of application needle 21 is immersed in application material 70 stored in application material container 22 is obtained. Subsequently, X-axis table 11 and Y-axis table 12 are operated to position carrier 6 in the X-axis direction and the Y-axis direction such that the region where detection portion 3 is to be formed first is disposed immediately below application mechanism 14. Subsequently, Z-axis table 13 is operated to lower Z-axis table 13 and application mechanism 14 by a distance d in the Z-axis direction such that the tip of application needle 21 is pushed downward below the upper surface of carrier 6 when the application needle is in the second state.

Subsequently, servomotor 41 of application mechanism 14 is operated to switch from the first state to the second state. Specifically, the rotation shaft of servomotor 41 is rotated by operating servomotor 41 to rotate cam 43. As a result, the height of the cam surface of cam 43 in the Z-axis direction changes, so that the position of bearing 44 in contact with the cam surface in the Z-axis direction also changes according to the rotation of the drive shaft of servomotor 41. Movable portion 46, application needle 21 holder fixing portion 47, application needle holder accommodation portion 48, and application needle holder 20 held by application needle holder accommodation portion 48 also move in the Z-axis direction according to the position change of bearing 44 in the Z-axis direction. As a result, application needle 21 moves in the Z-axis direction by operating servomotor 41, and the first state in FIG. 9 and the second state in FIG. 10 are switched. In application mechanism 14, the rotational motion of servomotor 41 can be converted into the motion (vertical motion) of application needle 21 in the Z-axis direction, so that application needle 21 can be quickly and accurately moved in the Z-axis direction.

In the first state of FIG. 9, application needle 21 is disposed at the uppermost position in the movable range. At this time, the tip of application needle 21 is immersed in application material 70 held in application material container 22. In the first state, the outer ring of bearing 44 is in contact with the upper end flat region of the cam surface of cam 43.

In the second state of FIG. 10, application needle 21 is disposed at the lowermost position in the movable range. At this time, the application material containing the capture antibody is held at the tip of application needle 21. Specifically, the application material containing the capture antibody is held on the end surface and the side surface of the tip of application needle 21. The tip of application needle 21 passes through the hole made in the bottom of application material container 22, protrudes downward from the bottom surface of application material container 22, and is pushed downward below the upper surface of carrier 6.

As described above, when servomotor 41 is operated to switch from the first state to the second state, recess 7 is formed in carrier 6, and at the same time, the capture antibody is applied to bottom surface 7A of recess 7. Subsequently, servomotor 41 is operated to switch from the second state to the first state.

Furthermore, after only X-axis table 11 and Y-axis table 12 are operated to dispose the region where detection portion 3 is to be formed second immediately below application mechanism 14, Z-axis table 13 is lowered by distance d, and then servomotor 41 of application mechanism 14 is operated to switch from the first state to the second state. Furthermore, after the second state is switched to the first state, Z-axis table 13 is raised by distance d.

By continuously repeating the above operation, the plurality of detection portions 3 are formed on the upper surface of carrier 6.

Advantageous Effect

The advantageous effects of immunochromatography assay kit 100 of the first embodiment will be described in comparison with the conventional immunochromatography assay kit (hereinafter, simply referred to as a first comparative example). In the first comparative example, the detection portion is formed on a flat plane, and provided such that color development in the detection portion derived from the labeled antibody is visually checked. For this reason, in the first comparative example, the sufficient area (for example, greater than or equal to several mm$^2$) of the detection portion is required so as not to be erroneously determined by the visual determination, and it is difficult to reduce the use amount of expensive capture antibody immobilized on the detection portion. As a result, in the first comparative example, it is difficult to reduce the manufacturing cost.

On the other hand, in immunochromatography assay kit 100, the dot width of each detection portion 3 can be made less than 1 mm by reducing the tip diameter of application needle 21. That is, in immunochromatography assay kit 100, the area of each detection portion 3 can be reduced as compared with the area of each detection portion in the first comparative example, the amount of the capture antibody immobilized on each detection portion 3 can be reduced as compared with the amount of the capture antibody immobilized on each detection portion in the first comparative example. As a result, the manufacturing cost of immunochromatography assay kit 100 can be reduced as compared with the manufacturing cost of the first comparative example.

Furthermore, according to immunochromatography assay kit 100, detection portion 3 is checked using the electron microscope, and the number of labeled antibodies captured by detection portion 3 in the electron microscope image is measured, whereby the detection target in the specimen can be quantitatively evaluated.

In addition, when the detection portion formed on the flat plane is miniaturized as in the first comparative example, for example, the labeled antibody is required to be checked by enlarging the detection portion with the microscope or the like, but it is difficult to search for and align the miniaturized minute detection portion with the microscope. As a countermeasure, a method for providing a mark on a kit and providing the detection portion at a predetermined distance from the mark is conceivable. However, in this case, equipment for providing the mark is required separately from equipment for forming the detection portion, and the number of processes is increased, so that manufacturing takt cannot be reduced, and it is difficult to reduce the cost.

On the other hand, in immunochromatography assay kit 100, the plurality of recesses 7 are formed in carrier 6, and each detection portion 3 includes bottom surface 7A of one recess 7. Therefore, when the labeling substance on detection portion 3 is directly checked using the electron microscope, the defocus caused by the distance between the upper surface and bottom surface 7A of carrier 6 can be checked in the microscope image of the electron microscope, so that recess 7 can be searched in the microscope image of the electron microscope using the defocus. As a result, in immunochromatography assay kit 100, each detection portion 3 can be miniaturized as compared with the first comparative example. For example, in immunochromatography assay kit 100, the dot width of each detection portion 3 can be made less than 1 mm by reducing the tip diameter of application needle 21. That is, in immunochromatography assay kit 100, the area of each detection portion 3 can be reduced as compared with the area of each detection portion in the first comparative example, the amount of the capture antibody immobilized on each detection portion 3 can be reduced as compared with the amount of the capture antibody immobilized on each detection portion in the first comparative example. As a result, the manufacturing cost of immunochromatography assay kit 100 can be reduced as compared with the manufacturing cost of the first comparative example.

Furthermore, the image on detection portion 3 can be easily focused by focusing the image on bottom surface 7A. That is, in immunochromatography assay kit 100, the time required for searching detection portion 3 can be shortened as compared with the case where each detection portion 3 does not include bottom surface 7A of one recess 7.

In addition, in immunochromatography assay kit 100, unlike the first comparative example, the mark used for searching detection portion 3 is not required to be separately provided, and the equipment for providing the mark separately from the equipment for forming the detection portion is not required to be provided. Furthermore, in immunochromatography assay kit 100, recess 7 can be formed simultaneously with detection portion 3, so that the manufacturing tact can be reduced as compared with the case where the mark is provided in the first comparative example.

In immunochromatography assay kit 100, the width of each detection portion can be reduced less than or equal to 100 μm. In such immunochromatography assay kit 100, the amount of the capture antibody immobilized on each detection portion 3 is greatly reduced as compared with the amount of the capture antibody immobilized on each detection portion in the first comparative example, so that the manufacturing cost of immunochromatography assay kit 100 can be greatly reduced as compared with the manufacturing cost of the first comparative example.

Immunochromatography assay kit 100 includes the plurality of detection portions 3. In such immunochromatography assay kit 100, the labeling substance of the plurality of detection portions 3 can be checked in the electron microscope image as compared with the immunochromatography assay kit including only one detection portion 3, so that reliability of an assay result is improved.

In immunochromatography assay kit 100, the plurality of detection portions 3 are arranged one-dimensionally with respect to developing direction D. In such immunochromatography assay kit 100, as compared with an immunochromatography assay kit in which the plurality of detection portions 3 are randomly disposed, the detection target efficiently flows to all detection portions 3 and binds to the capture antibody, so that the stable assay result can be obtained.

In immunochromatography assay kit 100, the shortest distance between two adjacent detection portions among the plurality of detection portions 3 is less than 1 mm. In such immunochromatography assay kit 100, the plurality of detection portions 3 can be observed even in the relatively small view field as compared with an immunochromatography assay kit in which the shortest distance is greater than or equal to 1 mm, so that each detection portion 3 can be easily searched.

The operational effects of the method for manufacturing immunochromatography assay kit 100 of the first embodiment will be described in comparison with a manufacturing method (hereinafter, simply referred to as a second comparative example) in which each detection portion 3 is formed using a dispenser and a manufacturing method (hereinafter, simply referred to as a third comparative example) in which each detection portion 3 is formed by an inkjet method.

In the second and third comparative examples, in order to form detection portion 3 with a minute size, the opening width of the tip of the dispenser or the nozzle is required to be reduced. However, when application material 70 having high viscosity is used, application material 70 cannot be discharged, and clogging may be generated. In the third comparative example, in the method for discharging the liquid material containing the capture antibody by instantaneously increasing the pressure in the container using a piezo element or the like, the discharge pressure is high, so that there is a problem that the liquid material is likely to spread when landing on carrier 6, and the shape of detection portion 3 is not stable.

On the other hand, in the method for manufacturing immunochromatography assay kit 100, the tip diameter of application needle 21 is only required to be reduced in order to form minute detection portion 3, so that the clogging as in the comparative examples 2, 2 is not generated regardless of the viscosity. Furthermore, in the above manufacturing method, because the position in the Z-axis direction of the tip of application needle 21 with respect to the upper surface of carrier 6 can be precisely controlled by Z-axis table 13, variations in the size of detection portion 3 can be reduced, and immunochromatography assay kit 100 can be stably manufactured.

In addition, in the second comparative example, in order to apply the droplets, it is difficult to stably form detection portion 3 having the dot width less than 1 mm, particularly to stably form detection portion 3 having the dot width of less than 100 μm.

On the other hand, in the method for manufacturing immunochromatography assay kit 100, since application needle 21 is used, immunochromatography assay kit 100 in which the planar outer shape of each detection portion 3 is the dot shape and the width of each detection portion 3 is less than 1 mm can be easily and stably manufactured.

Furthermore, in the method for manufacturing immunochromatography assay kit 100, recess 7 is formed in carrier 6 using application needle 21 while the capture antibody is applied to bottom surface 7A of recess 7, so that formation of detection portion 3 including bottom surface 7A of one recess 7 and the application of the capture antibody can be performed by one operation. Thus, the tact time does not increase due to the formation of detection portion 3, and the manufacturing cost does not increase.

<First Modification>

Immunochromatography assay kit 100 of the first embodiment may adopt the following modifications.

Detection area t may include at least one detection portion 3.

In immunochromatography assay kit 100, detection portions 3 have the same configuration, but the present invention is not limited thereto. In immunochromatography assay kit 100, the concentration of the capture antibody immobilized on each of detection portions 3 is constant, but the concentration of the capture antibody immobilized on each of detection portions 3 may be different from each other. For example, the concentration of the capture antibody may be provided to gradually decrease from one side toward the other side in the direction orthogonal to developing direction D. In addition, a set of patterns including the plurality of detection portions 3 having different concentrations of the capture antibody may be arranged side by side. The plurality of detection portions 3 can be easily formed using a plurality of application mechanisms 14 having different concentrations of the capture antibody in the application material stored in application material container 22.

In addition, at least one of the planar outer shape of each of detection portions 3, the dot width of each of detection portions 3, the distance between two adjacent detection portions 3, the planar outer shape of bottom surface 7A of each of recesses 7, the maximum width of each of bottom surfaces 7A, and the depth of each of bottom surfaces 7A may be different from each other. Such the plurality of detection portions 3 can be easily formed using a plurality of kinds of application needles 21 or using a plurality of kinds of application conditions.

In immunochromatography assay kit 100, the plurality of recesses 7 are formed in detection region t of carrier 6, and one detection portion 3 includes bottom surface 7A of one recess 7, but the present invention is not limited thereto.

Each detection portion 3 may include entire bottom surface 7A of each recess 7 and at least a part of wall surface 7B. Each detection portion 3 may include entire bottom surface 7A and wall surface 7B of each recess 7. In addition, each detection portion 3 may include entire bottom surface 7A and wall surface 7B of each recess 7, and an annular region continuous with wall surface 7B of the upper surface of carrier 6.

Figure 11:
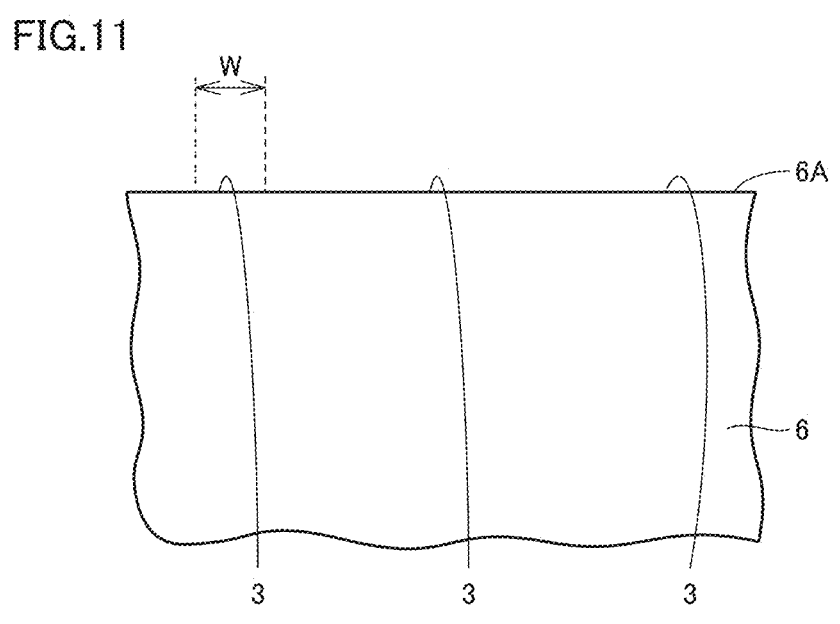

The plurality of detection portions 3 may include at least one detection portion 3 in FIG. 4 and at least one detection portion 3 in FIG. 11. The plurality of detection portions 3 in FIG. 11 include only the upper surface of carrier 6. Application material 70 attached to the tip or the tip of application needle 21 in the above manufacturing method comes into contact with the upper surface of carrier 6 and then moves upward without being pushed downward, so that detection portion 3 can be easily formed. In addition, all of detection portions 3 may be configured as detection portion 3 in FIG. 11. That is, the plurality of recesses 7 may not be formed in detection region t of carrier 6.

Figure 12:
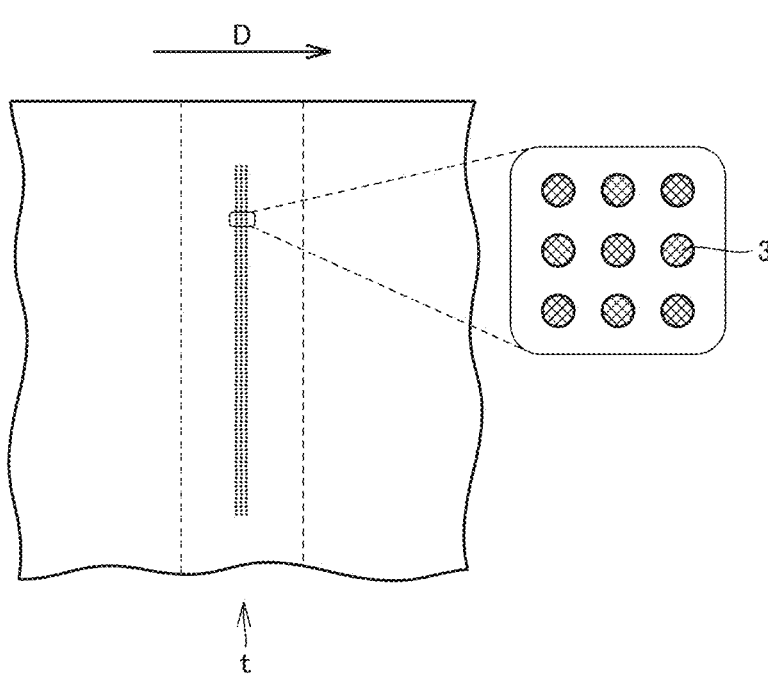
FIG. 12 is a partially enlarged plan view illustrating another modification of the detection portion in FIG. 2.

As illustrated in FIG. 12, in immunochromatography assay kit 100, the plurality of detection portions 3 may be arranged at intervals in developing direction D. For example, the distance between two adjacent detection portions 3 in developing direction D is equal to the distance between two adjacent detection portions 3 in the direction orthogonal to developing direction D.

In the method for manufacturing immunochromatography assay kit 100, one application needle 21 is used to form the plurality of detection portions 3, but the plurality of application needles 21 may be used to form the plurality of detection portions 3. In other words, the application device may include the plurality of application mechanisms 14.

In addition, in order to further increase the accuracy in the application process of application material 70 by application needle 21, the moving speed of application needle 21 in the Z-axis direction may be changed according to the position of application needle 21. For example, when the first state is switched to the second state, the moving speed of application tion needle 21 decreases before the second state is implemented. The decrease of the moving speed of application needle 21 is implemented by decreasing the rotational speed of servomotor 41.

By performing such control, the moving speed of application needle 21 is sufficiently low when application needle 21 comes into contact with carrier 6, so that the contact time between the tip of application needle 21 or application material 70 attached to the tip and carrier 6 can be lengthened. For this reason, the amount of the capture antibody applied to carrier 6 increases and the concentration increases, so that the antigen-antibody reaction with the detection target can be further stabilized.

In immunochromatography assay kit 100, specimen dropping portion 1 and conjugate portion 2 may be formed on the single porous member separated from carrier 6. In immunochromatography assay kit 100, conjugate portion 2 may be formed on carrier 6, and specimen dropping portion 1 may be formed on the porous member separated from carrier 6. In immunochromatography assay kit 100, absorption portion 5 may be formed on carrier 6.

Second Embodiment

Figure 13:
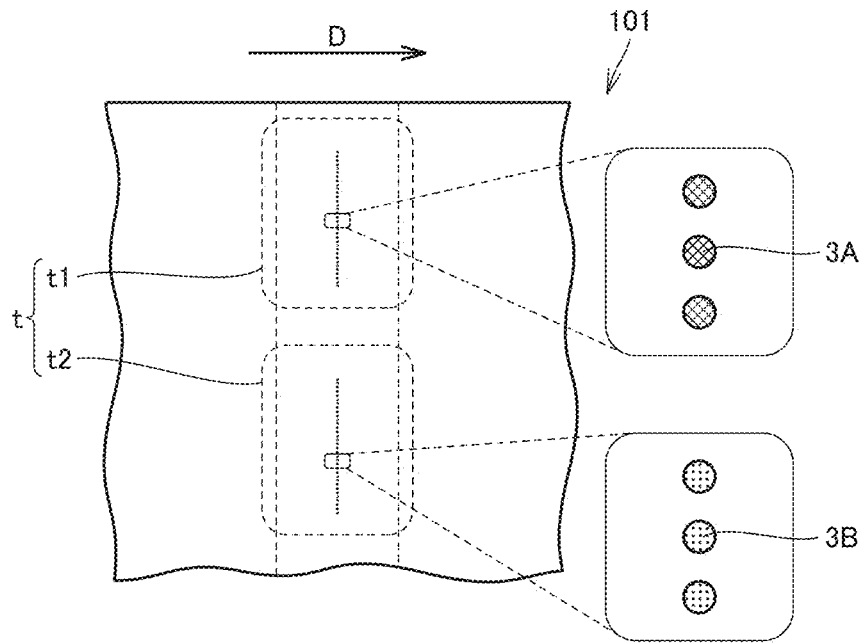
FIG. 13 is a partially enlarged plan view illustrating a detection portion of an immunochromatography assay kit according to a second embodiment.

An immunochromatography assay kit 101 according to a second embodiment has a configuration basically similar to that of immunochromatography assay kit 100 according to the first embodiment, and exhibits the similar effect, but is different from immunochromatography assay kit 100 in that the plurality of detection portions 3 include a first detection portion 3A and a second detection portion 3B as illustrated in FIG. 13.

A first capture antibody having a property of binding to a first type of detection target is immobilized on first detection portion 3A. A second capture antibody having a property of binding to a second type of detection target different from the first type of detection target is immobilized on second detection portion 3B.

As illustrated in FIG. 13, for example, the plurality of detection portions 3 include a plurality of first detection portions 3A and a plurality of second detection portions 3B. The plurality of first detection portions 3A are arranged at intervals in the direction orthogonal to developing direction D. For example, the plurality of first detection portions 3A are arranged one-dimensionally. The plurality of second detection portions 3B are arranged at intervals in the direction orthogonal to developing direction D. For example, the plurality of second detection portions 3B are arranged one-dimensionally.

The plurality of first detection portions 3A and the plurality of second detection portions 3B are arranged at intervals in the direction orthogonal to developing direction D. The shortest distance between first detection portion 3A and second detection portion 3B is longer than the shortest distance between two adjacent first detection portions 3A and the shortest distance between two adjacent second detection portions 3B. For example, the plurality of first detection portions 3A and the plurality of second detection portions 3B are arranged one-dimensionally as a whole.

Each of first detection portion 3A and second detection portion 3B has the same configuration as each detection portion 3 in the first embodiment. For example, the dot width of first detection portion 3A is equal to the dot width of second detection portion 3B. For example, the dot width of first detection portion 3A may be narrower or wider than the dot width of second detection portion 3B.

In detection region t, the region in which the plurality of first detection portions 3A are arranged is divided into a first detection region t1 and the region in which the plurality of second detection portions 3B are arranged is divided into a second detection region t2. First detection region t1 and second detection region t2 are arranged side by side in the direction orthogonal to developing direction D.

Each first detection portion 3A includes bottom surface 7A of each recess 7. Each second detection portion 3B includes bottom surface 7A of each recess 7.

According to immunochromatography assay kit 101 of the second embodiment, two types of detection targets can be detected from the single specimen by immunochromatography.

Immunochromatography assay kit 101 can be manufactured in the same manner as the immunochromatography assay kit of the first embodiment. Preferably, the application device includes a first application mechanism 14 forming first detection portion 3A by applying the first capture antibody onto carrier 6, and a second application mechanism 14 forming second detection portion 3B by applying the second capture antibody onto carrier 6. First application mechanism 14 includes a first application needle 21 and a first application material container 22 in which the application material containing the first capture antibody is stored. Second application mechanism 14 includes a second application needle 21 and a second application material container 22 in which the application material containing the second capture antibody is stored.

In the method for manufacturing immunochromatography assay kit 101, first application needle 21 holds the first capture antibody at the tip thereof. Second application needle 21 holds the second capture antibody at the tip thereof. In the process of forming the plurality of detection portions 3, first detection portion 3A is formed by applying the first capture antibody to the first region of carrier 6 using first application needle 21. Furthermore, second detection portion 3B is formed by applying the second capture antibody to the second region of carrier 6 using second application needle 21.

When immunochromatography assay kit 101 is manufactured using such the application device, the number of manufacturing man-hour can be reduced as compared with the case of manufacturing immunochromatography assay kit 101 using one application device including only one application mechanism 14, and the manufacturing cost can be reduced as compared with the case of manufacturing immunochromatography assay kit 101 using the plurality of application devices including only one application mechanism 14.

<Second Modification>

Immunochromatography assay kit 101 of the second embodiment can also adopt a modification similar to immunochromatography assay kit 100 of the first embodiment.

Furthermore, immunochromatography assay kit 101 can adopt the following modifications.

Each of the plurality of first detection portions 3A and the plurality of second detection portions 3B may be alternately arranged.

Figure 14:
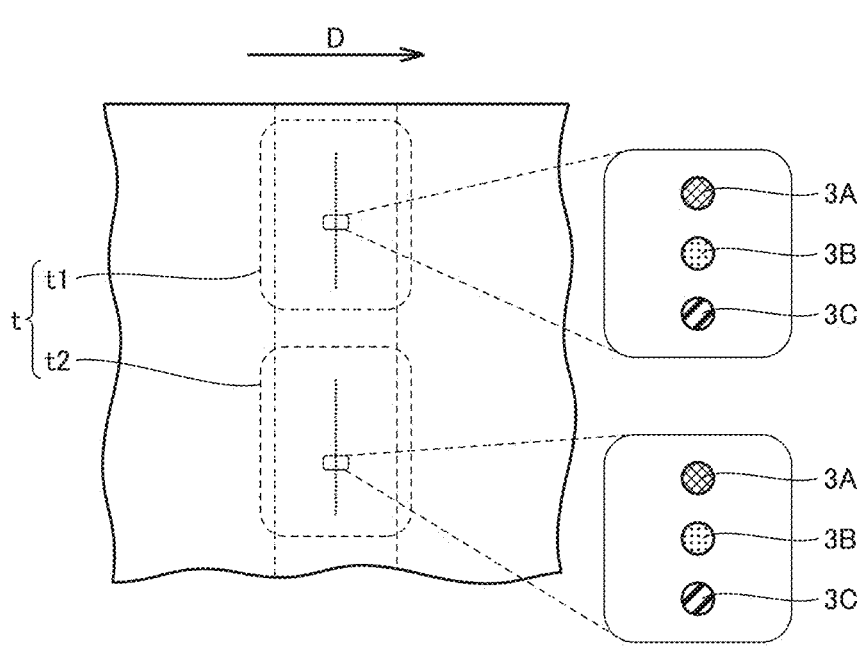
FIG. 14 is a partially enlarged plan view illustrating a modification of the detection portion in FIG. 13.
Figure 15:
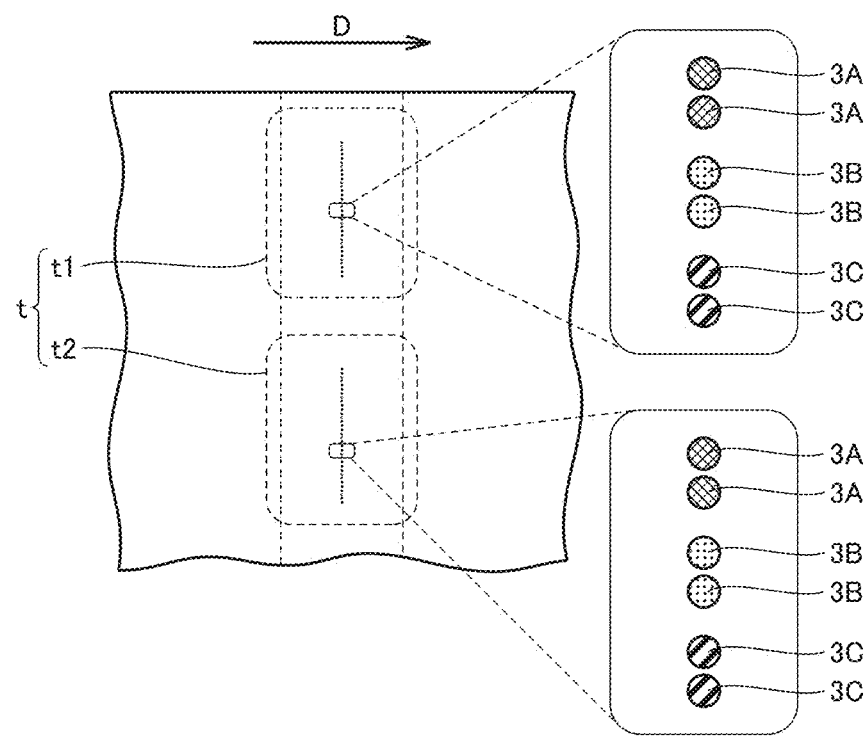
FIG. 15 is a partially enlarged plan view illustrating another modification of the detection portion in FIG. 13.
Figure 16:
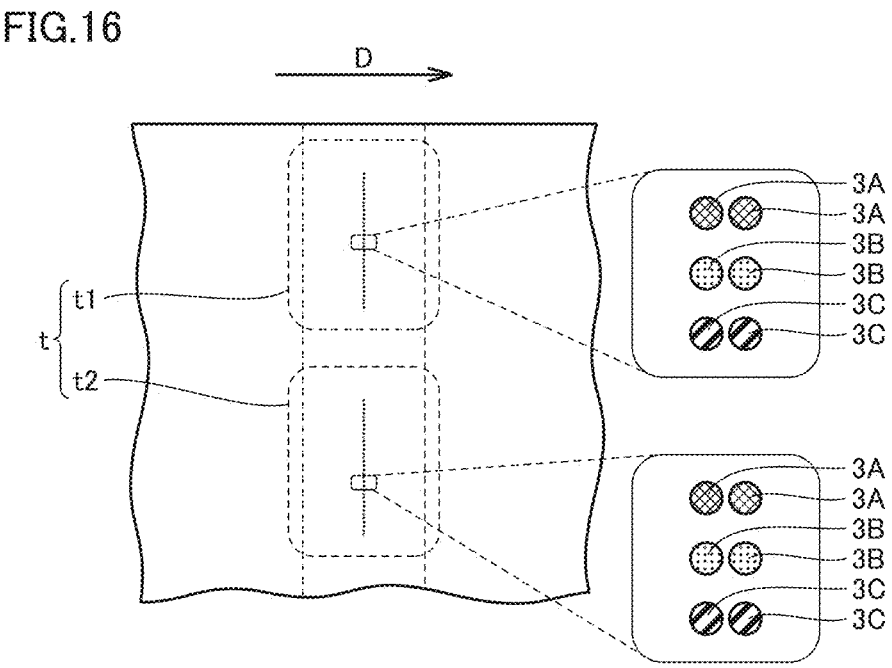
FIG. 16 is a partially enlarged plan view illustrating still another modification of the detection portion in FIG. 13.

As illustrated in FIGS. 14 to 16, the plurality of detection portions 3 may further include a plurality of third detection portions 3C in addition to first detection portion 3A and second detection portion 3B. A third capture antibody having a property of binding to a third type of detection target different from the first type of detection target and the second type of detection target is immobilized on each of third detection portions 3C.

As illustrated in FIG. 14, the plurality of first detection portions 3A, the plurality of second detection portions 3B, and the plurality of third detection portions 3C are alternately arranged one by one, for example, in the direction orthogonal to developing direction D.

As illustrated in FIG. 15, the plurality of first detection portions 3A, the plurality of second detection portions 3B, and the plurality of third detection portions 3C are alternately arranged, for example, in the direction orthogonal to developing direction D. In this case, for example, the distance between two adjacent first detection portions 3A and the distance between two adjacent second detection portions 3B are shorter than the distance between adjacent first detection portion 3A and second detection portion 3B. For example, the distance between two adjacent second detection portions 3B and the distance between two adjacent third detection portions 3C are shorter than the distance between the adjacent second detection portion 3B and third detection portion 3C.

As illustrated in FIG. 16, for example, each of the plurality of first detection portions 3A, the plurality of second detection portions 3B, and the plurality of third detection portions 3C are one-dimensionally arranged in developing direction D. Furthermore, the plurality of first detection portions 3A, the plurality of second detection portions 3B, and the plurality of third detection portions 3C are alternately arranged one by one in the direction orthogonal to developing direction D. For example, the distance between first detection portion 3A and second detection portion 3B adjacent to each other in the direction orthogonal to developing direction D is longer than the distance between two adjacent first detection portions 3A and the distance between two adjacent second detection portions 3B in developing direction D. For example, the distance between second detection portion 3B and third detection portion 3C adjacent to each other in the direction orthogonal to developing direction D is longer than the distance between two second detection portions 3B adjacent to each other in developing direction D and the distance between two third detection portions 3C adjacent to each other in developing direction D.

In the modification illustrated in FIGS. 14 to 16, in one set of first detection portion 3A, second detection portion 3B, and third detection portion 3C, at least one of the planar outer shape of each detection portion 3, the dot width of each detection portion 3, the distance between two adjacent detection portions 3, the planar outer shape of bottom surface 7A of each recess 7, the maximum width of each bottom surface 7A, and the depth of each bottom surface 7A may be different from each other.

For example, the dot width of second detection portion 3B may be narrower than the dot width of first detection portion 3A and wider than the dot width of third detection portion 3C. The maximum width of bottom surface 7A included in second detection portion 3B may be narrower than the maximum width of bottom surface 7A included in first detection portion 3A and wider than the maximum width of bottom surface 7A included in third detection portion 3C.

The planar outer shape of second detection portion 3B may be rectangular, and the planar outer shape of each detection portion 3 of first detection portion 3A and third detection portion 3C may be circular.

The depth of bottom surface 7A included in second detection portion 3B may be shallower than the maximum width of bottom surface 7A included in first detection portion 3A and deeper than the maximum width of bottom surface 7A included in third detection portion 3C.

The distance between first detection portion 3A and second detection portion 3B may be longer than the distance between second detection portion 3B and third detection portion 3C and the distance between third detection portion 3C and first detection portion 3A.

First detection portion 3A, second detection portion 3B, and third detection portion 3C can be easily formed using a plurality of kinds of application needles 21 or using a plurality of kinds of application conditions.

In this way, first detection portion 3A, second detection portion 3B, and third detection portion 3C can be easily identified in one visual field.

Third Embodiment

An immunochromatography assay kit 102 according to a third embodiment has a configuration basically similar to that of immunochromatography assay kit 100 according to the first embodiment and exhibits a similar effect, but is different from immunochromatography assay kit 100 in that specimen dropping portion 1 and conjugate portion 2 are formed on carrier 6. That is, in immunochromatography assay kit 102, specimen dropping portion 1, conjugate portion 2, the plurality of detection portions 3, and control portion 4 are formed on the upper surface of the single porous member (one carrier 6).

Figures 17, 18:
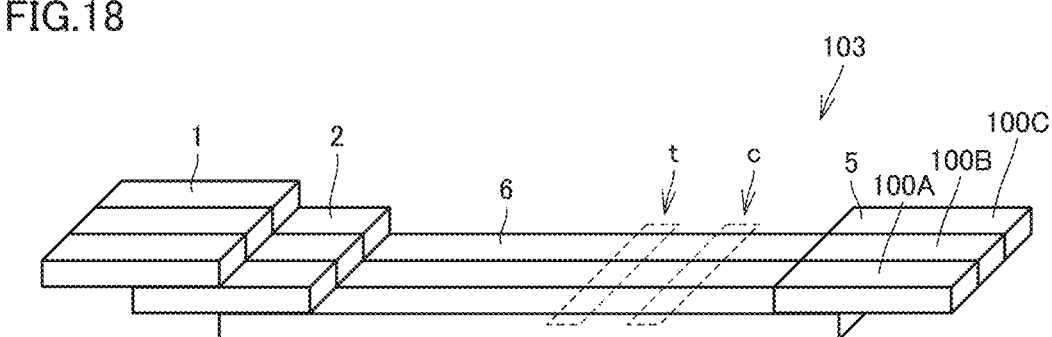
FIG. 17 is a perspective view illustrating an immunochromatography assay kit according to a third embodiment.
FIG. 18 is a perspective view illustrating an immunochromatography assay kit according to a fourth embodiment.

In immunochromatography assay kit 102 of FIG. 17, absorption portion 5 is also formed on carrier 6.

Specimen dropping portion 1 is the region where the specimen is dropped on carrier 6, and is disposed on one side in developing direction D. Conjugate portion 2 is the region in which the labeled antibody is applied to the upper surface of carrier 6, and is disposed between specimen dropping portion 1 and detection region t in developing direction D. Absorption portion 5 is the region in which the surplus specimen is absorbed in carrier 6, and is disposed on the other side in developing direction D with respect to control region C.

According to immunochromatography assay kit 102, the number of parts is reduced as compared with immunochromatography assay kit 100, so that the manufacturing cost of immunochromatography assay kit 102 can be reduced as compared with the manufacturing cost of immunochromatography assay kit 100.

<Third Modification>

Immunochromatography assay kit 102 of the third embodiment can also adopt modifications similar to immunochromatography assay kit 100 of the first embodiment and immunochromatography assay kit 101 of the second embodiment.

Fourth Embodiment

The immunochromatography assay kit 103 according to a fourth embodiment has a configuration basically similar to that of immunochromatography assay kit 100 according to the first embodiment, and exhibits a similar effect, but is different from immunochromatography assay kit 100 in that a plurality of immunochromatography assay kits 100A to 100C are configured as a connection body connected in the direction orthogonal to developing direction D as illustrated in FIG. 18. The detection targets of immunochromatography assay kits 100A to 100C are different from each other.

Each of immunochromatography assay kits 100A to 100C may be fixed to each other by an arbitrary method, and for example, is bonded.

According to immunochromatography assay kit 103 of the fourth embodiment, three types of detection targets can be detected by immunochromatography using one immunochromatography assay kit 103 configured as the connection body.

Example 1

In Example 1, an observation result using the electron microscope of detection portion 3 of immunochromatography assay kit 100 will be described.

<Sample>

Carrier 6 was the porous member made of nitrocellulose. Each of detection portions 3 was formed to include bottom surface 7A of recess 7 using application needle 21 having the truncated conical shape at the tip and the tip diameter of 50 µm.

<Observation Method>

Figure 19:
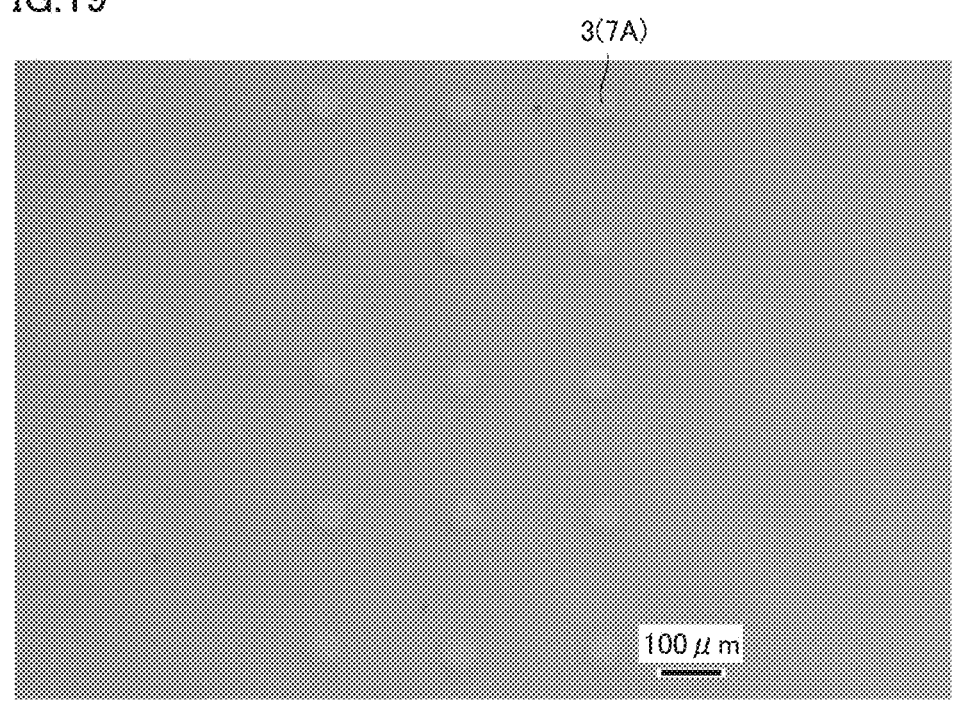
FIG. 19 is an electron microscope image obtained by observing a detection portion 3 of a first example using an electron microscope.

FIG. 19 is a microscopic image obtained by observing detection portion 3 of the sample using the microscope.

As illustrated in FIG. 19, in the microscopic image, because a difference is generated between the background and detection portion 3 due to the defocus caused by recess 7, bottom surface 7A of recess 7 can be easily searched, and minute detection portion 3 including bottom surface 7A can be easily searched.

Example 2

In Example 2, an immunochromatography result using immunochromatography assay kit 100 will be described.

<Sample>

Specimen dropping portion 1 and conjugate portion 2 were glass fiber pads. Carrier 6 was the porous member made of nitrocellulose. Each of detection portions 3 was formed to include bottom surface 7A of recess 7 using application needle 21 having the truncated conical shape at the tip and the tip diameter of 50 µm.

<Assay Method>

The assay method was equivalent to the assay method of the immunochromatography assay kit described above.

Figure 20:
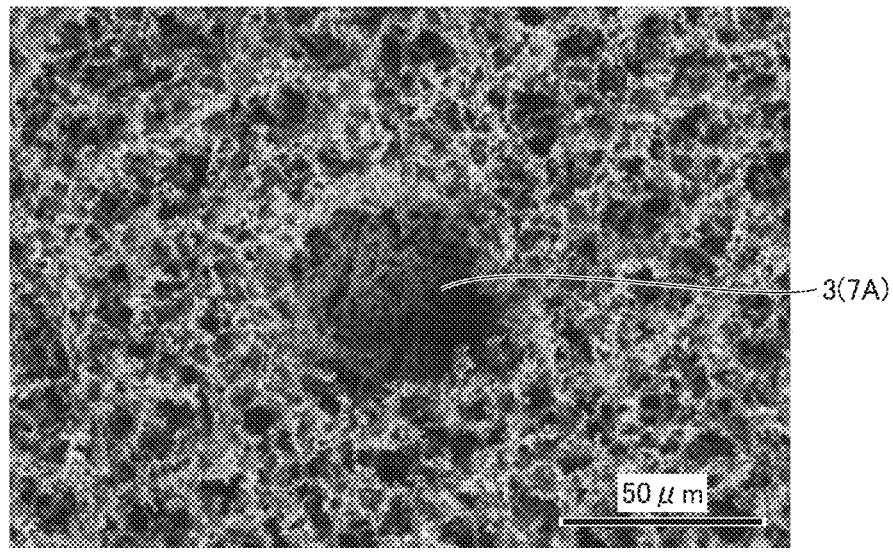
FIG. 20 is an electron microscope image obtained by observing the detection portion 3 of a second example using the electron microscope.

FIG. 20 is an electron microscope image obtained by observing detection portion 3 of the sample using the electron microscope.

As illustrated in FIG. 20, since contrast of brightness and darkness caused by recess 7 is generated in the electron microscope image, bottom surface 7A of recess 7 can be easily searched, and minute detection portion 3 including bottom surface 7A can be easily searched.

Figure 21:
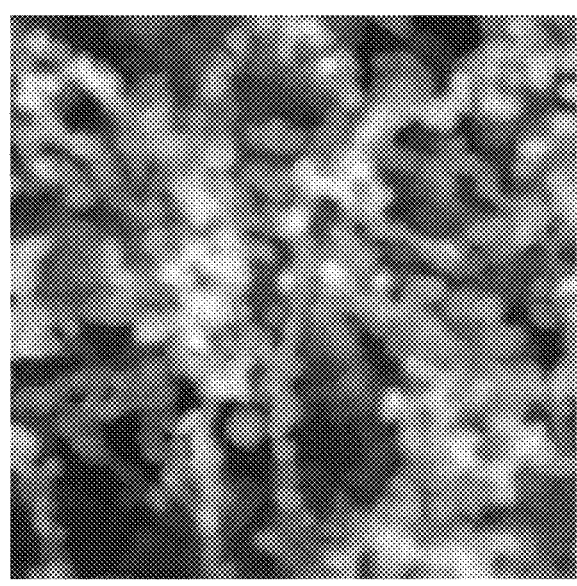
FIG. 21 is an electron microscope image obtained by observing the detection portion 3 before an auxiliary liquid is dropped using the electron microscope in the second example.
Figure 22:
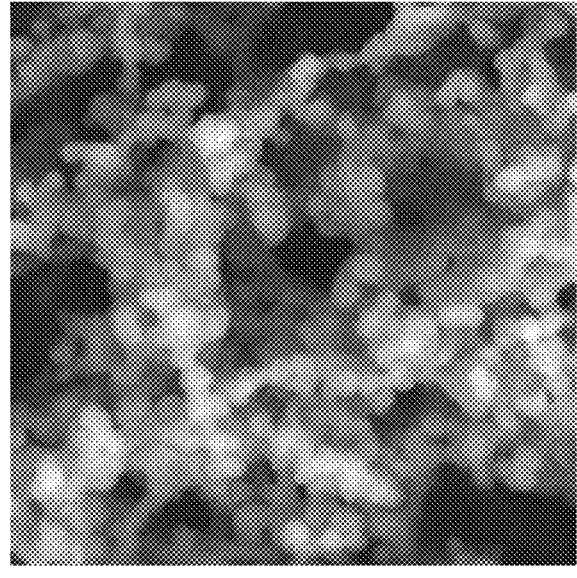
FIG. 22 is an electron microscope image obtained by observing the detection portion 3 after the auxiliary liquid is dropped using an electron microscope in the second example.

FIG. 21 is an electron microscope image of detection portion 3 before the auxiliary liquid is dropped, and FIG. 22 is an electron microscope image of detection portion 3 after the auxiliary liquid is dropped.

In the image of FIG. 22, it was checked that the edge of the image is clear as compared with the image in FIG. 21.

It should be considered that the disclosed embodiments and examples are an example in all respects and not restrictive. The scope of the present invention is defined by not the description above, but the claims, and it is intended that all modifications within the meaning and scope equivalent to the claims ae included in the present invention.

REFERENCE SIGNS LIST

1: specimen dropping portion, 2: conjugate portion, 3: detection portion, 3A: first detection portion, 3B: second detection portion, 3C: third detection portion, 4: control portion, 5: absorption portion, 6: carrier, 7: recess, 7A: bottom surface, 7B: wall surface, 11: X-axis table, 12: Y-axis table, 13: Z-axis table, 14: application mechanism, 15: observation optical system, 16: camera, 17: operation panel, 18: monitor, 19: control computer, 20: application needle holder, 21: application needle, 22: application material container, 41: servomotor, 42: frame, 43: cam, 44: bearing, 45: cam coupling plate, 46: movable portion, 47: application needle holder fixing portion, 48: application needle holder accommodation portion, 49: linear guide, 50: spring, 51, 52: fixing pin, 70: application material, 100, 100A, 100C, 101, 102, 103: immunochromatography assay kit

The invention claimed is:

1. An immunochromatography assay kit comprising:
a specimen dropping portion;
a conjugate portion on which a labeled antibody having a property of binding to a detection target in the specimen is immobilized; and
a detection portion to which a capture antibody having a property of binding to the detection target is attached,
wherein the specimen dropping portion, the conjugate portion, and the detection portion are formed on a porous member, and
wherein a cross-sectional shape of the detection portion is a recess which includes a bottom surface and opposing wall surfaces on either side of the bottom surface.

2. An immunochromatography assay kit comprising:
a specimen dropping portion;
a conjugate portion to which a labeled antibody having a property of binding to a detection target in the specimen is attached; and
at least one detection portion to which a capture antibody having a property of binding to the detection target is attached,
wherein the specimen dropping portion, the conjugate portion, and the at least one detection portion are formed on a porous member,
at least one recess is formed in the porous member, and
the at least one detection portion includes a bottom surface of the at least one recess.

3. The immunochromatography assay kit according to claim 1, wherein a width of the at least one detection portion is less than 1 mm.

4. The immunochromatography assay kit according to claim 1, wherein the width of the at least one detection portion is less than or equal to 100 μm.

5. The immunochromatography assay kit according to claim 1, wherein the at least one detection portion is a plurality of detection portions.

6. The immunochromatography assay kit according to claim 5, wherein the plurality of detection portions are arranged one-dimensionally or two-dimensionally.

7. The immunochromatography assay kit according to claim 5, wherein a shortest distance between two adjacent detection portions among the plurality of detection portions is less than 1 mm.

8. The immunochromatography assay kit according to claim 5, wherein the plurality of detection portions include a first detection portion to which a first capture antibody having a property of binding to the detection target of a first type is immobilized and a second detection portion to which a second capture antibody having a property of binding to the detection target of a second type is immobilized.

9. The immunochromatography assay kit according to claim 1, wherein the specimen dropping portion, the conjugate portion, and the at least one detection portion are formed on a single porous member.

10. The immunochromatography assay kit according to claim 1, wherein the specimen dropping portion, the conjugate portion, and the at least one detection portion are formed on a plurality of the porous members.

11. The immunochromatography assay kit according to claim 2, wherein a width of the at least one detection portion is less than 1 mm.

12. The immunochromatography assay kit according to claim 2, wherein the width of the at least one detection portion is less than or equal to 100 μm.

13. The immunochromatography assay kit according to claim 2, wherein the at least one detection portion is a plurality of detection portions.

14. The immunochromatography assay kit according to claim 2, wherein the at least one detection portion is a plurality of detection portions.

15. The immunochromatography assay kit according to claim 3, wherein the at least one detection portion is a plurality of detection portions.

16. The immunochromatography assay kit according to claim 1, wherein the cross-sectional shape of the detection portion is a tapered shape in which the interval between the opposing wall surfaces becomes narrower as approaching the bottom surface.

* * * * *